Dec. 16, 1947. W. B. CLARKE Plant Pat. 768
LILAC PLANT
Filed Dec. 4, 1946
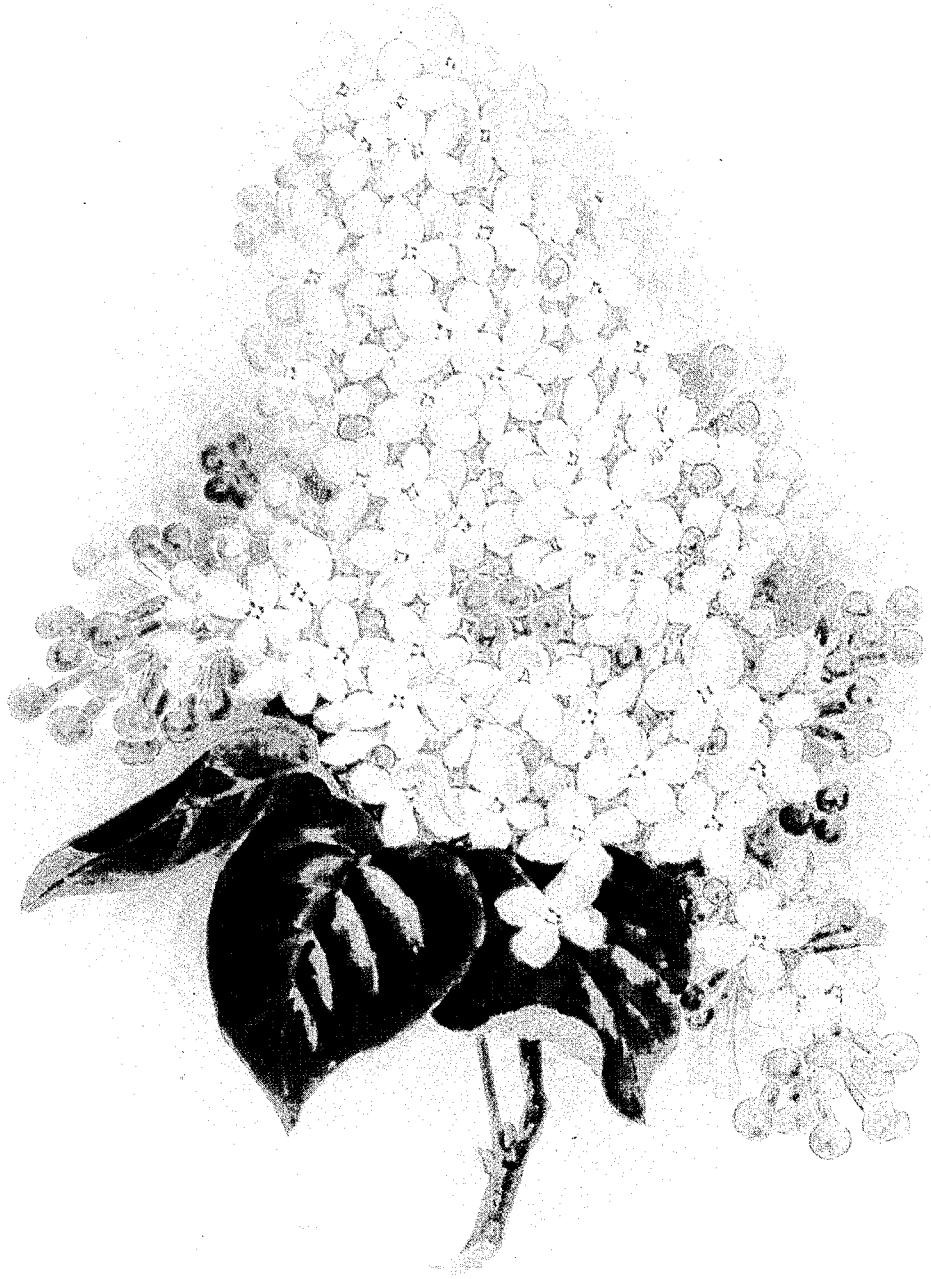
WITNESS
Addison J. Avery
INVENTOR
WALTER B. CLARKE,
by Rummler Rummler & Davis,
ATTYS.

Patented Dec. 16, 1947

Plant Pat. 768

UNITED STATES PATENT OFFICE

768

LILAC PLANT

Walter Bosworth Clarke, San Jose, Calif., assignor to W. B. Clarke & Co., San Jose, Calif., a partnership Application December 4, 1946, Serial No. 713,862

1 Claim. (Cl. 47—60)

The present discovery relates to a new and distinct variety of *Syringa vulgaris* plant, resulting from a cross made by me between an unnamed seedling as the pollen parent and a variety named "Mme. Francisque Morel" as the seed parent. This new variety has been reproduced from buds through several generations and its characteristics appear to be permanently fixed.

This new variety of lilac is the result of prolonged breeding efforts—extending over a period of fifteen years—to produce a pure pink lilac, not merely a lavender pink shade, but an attractive rose tone, that would combine all of the remarkable and unusual growth and desirable qualities of the finest lilacs. I believe that this lilac is unique in color and is the nearest to a true pink single-petaled lilac that is known.

Another distinct characteristic of this new variety is the red coloring of the buds as the petals begin to unfurl, which gradually shades off into the distinctive pink tone as the flower expands.

In general plant structure, this new variety is similar to the well-known *Syringa vulgaris*. The individual flower has the usual, small, bell-shaped, four-toothed calyx, but has a long salver-form, four-lobed corolla. Its panicles are large in size, are usually forked and rather broad for their length. The individual floret is approximately ⅞ to 1 inch in diameter across the petal tips. Its habit of growth is unusually vigorous. It blooms profusely in the spring of the year; the first blooms appear about April 15. The stems are long because of its very vigorous growth.

The accompanying painting shows the approximate shape of a single panicle, and its distinctive coloring.

The flower trusses present a distinctive compact conoidal mass of pink which is made more conspicuous by the reddish shade of the buds. The broad full thyrses on the upright sturdy stems are outstanding and noticeable. The abundant quantity of dark green foliage forms a pleasing contrast for the pink blooms. The flowers have a delicate fragrance.

The following is a detailed tabular description of this new variety.

Parentage: Seedling.

*Seed parent.*—Mme. Francisque Morel.

*Pollen parent.*—Unknown.

Classification: *Syringa vulgaris.*

Blooming habit:

*Blooms.*—Once in midseason, profusely. Vigorous grower.

*Panicles.*—Usually forked with rounded tips. Size.—moderately large. Shape.—usually forked and rather broad for length.

*Petalage.*—Single (4 corolla lobes).

*Floret.*—⅞ to 1 inch in diameter.

*Bud.*—Size—medium. Color—when petals begin to unfurl, red.

*Stems.*—Long.

*Leaves.*—Texture—leathery. Shape—usual.

*Stamens.*—Either sunk in the corolla tube or occasionally barely show at its top.

The color designations according to "A Dictionary of Color by Maerz and Paul" are as follows:

| Section | Plate | Letter | No. |
|---|---|---|---|
| Body of flower | 49 | G | 1 |
| Eye in flower | 9 | L | 5 |
| Buds | 3 | J | 5 |
| Leaf | 21 | K | 9 |
| Stem | 15 | C | 3 |

The distinctive pink color of the petals may also be identified in the Horticultural Color Chart of the Royal Horticultural Society, of London, England, as No. 623/2, published in 1942.

This new variety of lilac is easily distinguished from other varieties by its unusual coloring and fullness of bloom.

Having thus disclosed the invention, I claim:

A new and distinct variety of *Syringa vulgaris* plant with features in combination substantially as shown and described, characterized by the red color of its buds progressively changing into the distinctive pink of the full-blown flowers, by its profuseness of bloom and compact mass of florets forming the panicles.

WALTER BOSWORTH CLARKE.